US012605082B2

(12) United States Patent (10) Patent No.: US 12,605,082 B2
Sahara et al. (45) Date of Patent: Apr. 21, 2026

(54) ELECTRONIC DEVICE, METHOD FOR CONTROLLING ELECTRONIC DEVICE, AND PROGRAM

(71) Applicant: KYOCERA Corporation, Kyoto (JP)

(72) Inventors: Tooru Sahara, Yokohama (JP); Jun Kuroda, Kodaira (JP); Kenji Yamamoto, Yokohama (JP); Takuya Homma, Yokohama (JP); Fangwei Tong, Fukuoka (JP)

(73) Assignee: KYOCERA Corporation, Kyoto (JP)

( * ) Notice: Subject to any disclaimer, the term of this patent is extended or adjusted under 35 U.S.C. 154(b) by 73 days.

(21) Appl. No.: 18/560,595

(22) PCT Filed: May 10, 2022

(86) PCT No.: PCT/JP2022/019853
§ 371 (c)(1),
(2) Date: Nov. 13, 2023

(87) PCT Pub. No.: WO2022/249881
PCT Pub. Date: Dec. 1, 2022

(65) Prior Publication Data
US 2024/0245317 A1 Jul. 25, 2024

(30) Foreign Application Priority Data
May 27, 2021 (JP) ................................ 2021-089576

(51) Int. Cl.
*A61B 5/05* (2021.01)
*A61B 5/0245* (2006.01)
*G01S 13/88* (2006.01)

(52) U.S. Cl.
CPC .............. *A61B 5/0245* (2013.01); *A61B 5/05* (2013.01); *G01S 13/88* (2013.01)

(58) Field of Classification Search
CPC .. A61B 5/00; A61B 5/02; A61B 5/024; A61B 5/0245; A61B 5/05; A61B 5/0507;
(Continued)

(56) References Cited

U.S. PATENT DOCUMENTS 11,051,703 B2 7/2021 Liu et al.
2018/0235481 A1* 8/2018 Liu ...................... A61B 5/0205
(Continued)

FOREIGN PATENT DOCUMENTS

EP 2323546 B1 3/2017
JP 2018153619 A 10/2018
(Continued)

*Primary Examiner* — Mark D Remaly
(74) *Attorney, Agent, or Firm* — Studebaker Brackett PLLC

(57) ABSTRACT

An electronic device includes a transmission antenna, a reception antenna, and a controller. The transmission antenna transmits a transmission wave. The reception antenna receives a reflected wave that is the transmission wave having been reflected. The controller detects a heartbeat of a subject that reflects the transmission wave, based on a transmission signal transmitted as the transmission wave and a reception signal received as the reflected wave. The controller forms a beam of the transmission wave in a direction of the subject to detect a heartbeat of the subject.

9 Claims, 7 Drawing Sheets

FROM RECEPTION UNIT    10

11 — DISTANCE FFT PROCESSING UNIT

12 — VELOCITY FFT PROCESSING UNIT

13 — DETERMINING UNIT

14 — ANGLE-OF-ARRIVAL ESTIMATING UNIT

15 — OSCILLATION SOURCE EXTRACTING UNIT

16 — OSCILLATION COMPONENT EXTRACTING UNIT

17 — OSCILLATION WAVEFORM CONVERTING UNIT

18 — HEARTBEAT DATA EXTRACTING UNIT — DETECTION RESULT

(58) Field of Classification Search
CPC ...... G01S 13/343; G01S 13/536; G01S 13/88;
G01S 7/415
See application file for complete search history.

(56) References Cited

U.S. PATENT DOCUMENTS

| 2019/0011549 | A1 | 1/2019 | Mercuri et al. |
| 2021/0076971 | A1 | 3/2021 | Oloumi et al. |

FOREIGN PATENT DOCUMENTS

| JP | 2019132850 | A | 8/2019 |
| JP | 2021001735 | A | 1/2021 |

* cited by examiner

FIG. 2

FROM RECEPTION UNIT                    10

11 —— DISTANCE
FFT PROCESSING UNIT

12 —— VELOCITY
FFT PROCESSING UNIT

13 —— DETERMINING UNIT

14 —— ANGLE-OF-ARRIVAL
ESTIMATING UNIT

15 —— OSCILLATION
SOURCE EXTRACTING UNIT

16 —— OSCILLATION COMPONENT
EXTRACTING UNIT

17 —— OSCILLATION WAVEFORM
CONVERTING UNIT

18 —— HEARTBEAT DATA
EXTRACTING UNIT                    DETECTION
RESULT

ELECTRONIC DEVICE, METHOD FOR CONTROLLING ELECTRONIC DEVICE, AND PROGRAM

CROSS-REFERENCE TO RELATED APPLICATIONS

This application claims priority from Japanese Patent Application No. 2021-89576 filed in Japan on May 27, 2021, the entire disclosure of which is incorporated herein by reference.

TECHNICAL FIELD

The present disclosure relates to an electronic device, a method for controlling an electronic device, and a program.

BACKGROUND OF INVENTION

For example, in fields such as automobile-related industries, a technology for measuring a distance or the like between a vehicle of interest and a predetermined object is regarded as important. Recently, various studies have been conducted particularly on a radar (Radio Detecting and Ranging) technology for measuring a distance or the like to an object such as an obstacle by transmitting a radio wave such as a millimeter wave and then receiving a reflected wave reflected off the object. Such a technology for measuring a distance or the like is expected to be more important in the future with progresses of a technology for assisting drivers in driving and an automated-driving-related technology for partially or entirely automating driving.

Various suggestions have been made for a technology for detecting the presence of a predetermined object by receiving a reflected wave of a radio wave that has been transmitted and reflected off the object. For example, Patent Literature 1 has proposed an estimation device that estimates a direction or the like in which a mobile object such as a person is located, by using a radio signal received by a plurality of reception antennas. For example, Patent Literature 2 has proposed a method of detecting a vital sign including at least one of a heart rate or a respiratory rate of a subject in a non-contact manner by using a radar technology.

CITATION LIST

Patent Literature

Patent Literature 1: Japanese Unexamined Patent Application Publication No. 2019-132850
Patent Literature 2: Japanese Unexamined Patent Application Publication No. 2018-153619

SUMMARY

In one embodiment, an electronic device includes a transmission antenna, a reception antenna, and a controller.
The transmission antenna transmits a transmission wave.
The reception antenna receives a reflected wave that is the transmission wave having been reflected.
The controller detects a heartbeat of a subject that reflects the transmission wave, based on a transmission signal transmitted as the transmission wave and a reception signal received as the reflected wave.
The controller forms a beam of the transmission wave in a direction of the subject to detect a heartbeat of the subject.

In one embodiment, a method for controlling an electronic device includes
transmitting a transmission wave from a transmission antenna,
receiving, from a reception antenna, a reflected wave that is the transmission wave having been reflected,
detecting a heartbeat of a subject that reflects the transmission wave, based on a transmission signal transmitted as the transmission wave and a reception signal received as the reflected wave, and
forming a beam of the transmission wave in a direction of the subject to detect a heartbeat of the subject.
In one embodiment, a program causes
an electronic device to execute
transmitting a transmission wave from a transmission antenna,
receiving, from a reception antenna, a reflected wave that is the transmission wave having been reflected,
detecting a heartbeat of a subject that reflects the transmission wave, based on a transmission signal transmitted as the transmission wave and a reception signal received as the reflected wave, and
forming a beam of the transmission wave in a direction of the subject to detect a heartbeat of the subject.

BRIEF DESCRIPTION OF THE DRAWINGS

FIG. 2 is a functional block diagram schematically illustrating a configuration of the electronic device according to the one embodiment.

DESCRIPTION OF EMBODIMENTS

Figure 1:
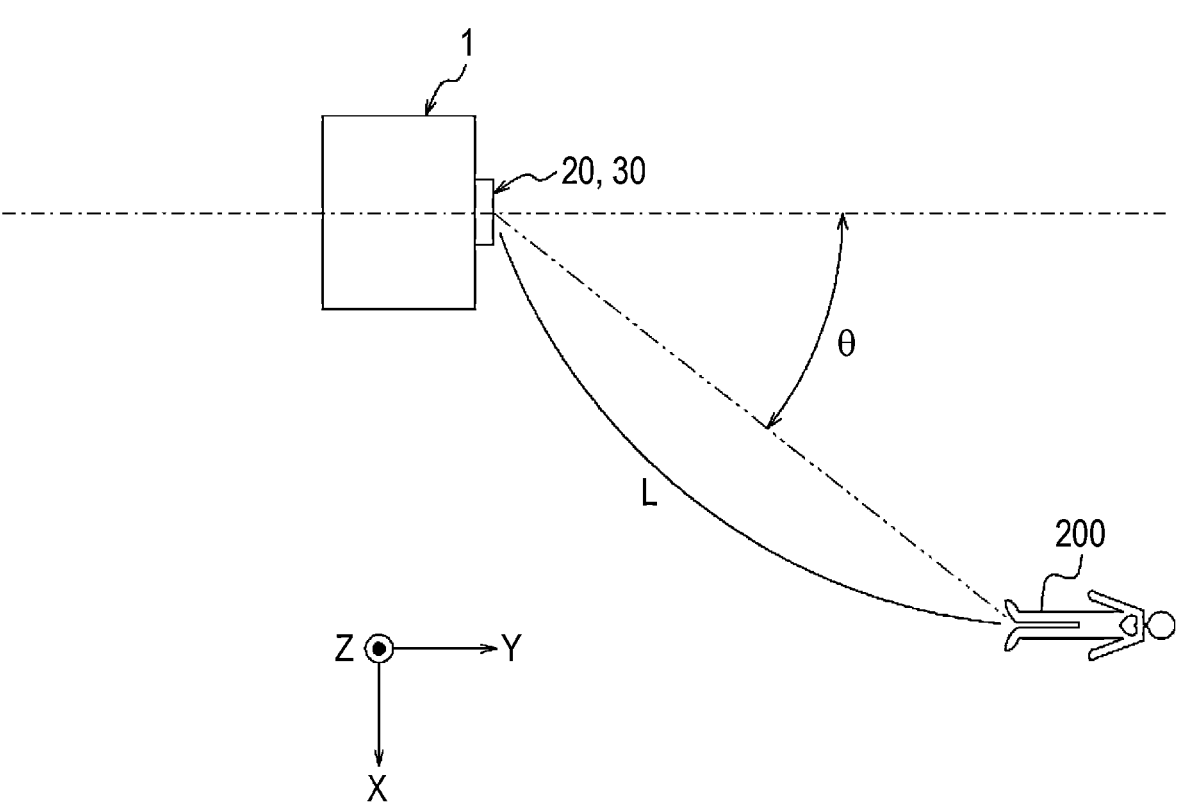
FIG. 1 is a diagram for describing how an electronic device according to one embodiment is used.

Convenience can be increased if a weak oscillation such as a heartbeat in a human body or the like can be detected with good accuracy through transmission and reception of a radio wave such as a millimeter wave, for example. The present disclosure provides an electronic device, a method for controlling an electronic device, and a program that enable a heartbeat in a human body or the like to be detected through transmission and reception of a radio wave. One embodiment can provide an electronic device, a method for controlling an electronic device, and a program that enable a heartbeat in a human body or the like to be detected through transmission and reception of a radio wave. One embodiment is described in detail below with reference to the drawings.

In the present disclosure, the term "electronic device" may refer to a device driven by electric power. The term "user" may refer to an entity (typically, a person) that uses a system and/or an electronic device according to one embodiment. The term "user" may also encompass an entity that monitors a subject such as a person by using the electronic device according to the one embodiment. The term "subject" may refer to an entity (for example, a person or an animal) to be monitored with the electronic device according to the one embodiment. The term "user" may encompass the subject.

The electronic device according to the one embodiment can detect a heartbeat of a subject such as a person located around the electronic device. Expected places where the electronic device according to the one embodiment is used may be, for example, specific facilities used by entities that perform social activities, such as a company, a hospital, a nursing home, a school, a gym, and a care facility. For example, in the case of a company, grasping and/or managing health conditions of employees and the like are extremely important. Likewise, in the case of a hospital, grasping and/or managing health conditions of patients, healthcare workers, and the like are extremely important. In the case of a nursing home, grasping and/or managing health conditions of residents, staff members, and the like are extremely important. The places where the electronic device according to the one embodiment is used are not limited to the aforementioned facilities such as a company, a hospital, and a nursing home, and may be any facility where grasping and/or managing health conditions of a subject are desired. Examples of the any facility may include a non-commercial facility such as a house of a user. The places where the electronic device according to the one embodiment is used are not limited to indoor places, and may be outdoor places. For example, the places where the electronic device according to the one embodiment is used may be the inside of mobility devices such as a train, a bus, and an airplane, a station, a landing, and the like. The places where the electronic device according to the one embodiment is used may be a mobility device such as an automobile, an aircraft, or a ship, a hotel, a house of a user, and a living room, a bathroom, a lavatory, a bedroom, or the like in the house.

For example, the electronic device according to the one embodiment may be used for the purpose of detecting or monitoring a heartbeat of a subject such as a person requiring medical care or a person requiring nursing care at a care facility or the like. For example, upon finding an abnormality in the heartbeat of the subject such as a person requiring medical care or a person requiring nursing care, the electronic device according to the one embodiment may issue a predetermined warning to, for example, the subject and/or another person. Thus, the electronic device according to the one embodiment allows, for example, the subject such as a person requiring medical care or a person requiring nursing care, for example, and/or a staff member at a care facility or the like to grasp that an abnormality is found in the pulse of the subject. On the other hand, upon finding no abnormality in the heartbeat of the subject such as a person requiring medical care or a person requiring nursing care (that is, finding the heartbeat normal), the electronic device according to the one embodiment may inform, for example, the subject and/or another person that no abnormality is found in the heartbeat. Thus, the electronic device according to the one embodiment allows, for example, the subject such as a person requiring medical care or a person requiring nursing care, for example, and/or a staff member at a care facility or the like to grasp that the pulse of the subject is normal.

The electronic device according to the one embodiment may detect the pulse of a subject other than a person, such as an animal. The description is given below on the assumption that the electronic device according to the one embodiment detects the pulse of a person with a sensor based on a technology such as a millimeter-wave radar, for example.

The electronic device according to the one embodiment may be installed in or on any stationary object or may be installed in or on any mobility device. The electronic device according to the one embodiment is capable of transmitting a transmission wave to an area around the electronic device from a transmission antenna. The electronic device according to the one embodiment is also capable of receiving a reflected wave that is the reflected transmission wave, from a reception antenna. The electronic device may include at least one of the transmission antenna or the reception antenna. Alternatively, for example, a radar sensor or the like may include at least one of the transmission antenna or the reception antenna.

A typical example is described below in which the electronic device according to the one embodiment is stationary. On the other hand, a subject whose pulse is detected by the electronic device according to the one embodiment may be stationary, may be moving, or may be moving their body while being stationary. Similarly to an ordinary radar sensor, the electronic device according to the one embodiment is capable of measuring a distance or the like between the electronic device and an object located around the electronic device when the object is movable. The electronic device according to the one embodiment is also capable of measuring a distance or the like between the electronic device and the object when both the electronic device and the object are stationary.

The electronic device according to the one embodiment is described in detail below with reference to the drawings. An example of how the electronic device according to the one embodiment detects an object is described.

FIG. 1 is a diagram for describing an example of how the electronic device according to the one embodiment is used. FIG. 1 illustrates an example of the electronic device according to the one embodiment that has functions of a sensor including a transmission antenna and a reception antenna.

As illustrated in FIG. 1, an electronic device 1 according to the one embodiment may include a transmission unit 20 and a reception unit 30 that are described later. As described later, the transmission unit 20 may include a transmission antenna. The reception unit 30 may include a reception antenna. Specific configurations of the electronic device 1, the transmission unit 20, and the reception unit 30 are described later. The electronic device 1 may appropriately include at least any of other functional units, such as at least part of a controller 10 (FIG. 2) included in the electronic device 1. The electronic device 1 may include at least any of other functional units, such as at least part of the controller 10 (FIG. 2) included in the electronic device 1, outside the electronic device 1. In FIG. 1, the electronic device 1 may be stationary without moving.

In the example illustrated in FIG. 1, the electronic device 1 includes a single transmission unit 20 including the transmission antenna and a single reception unit 30 including the reception antenna. However, the electronic device 1 may include, for example, multiple transmission units 20 and/or multiple reception units 30. As described later, the transmission unit 20 may include multiple transmission antennas. The reception unit 30 may include multiple reception antennas. A position where the transmission unit 20 and/or the reception units 30 are installed on the electronic device 1 is not limited to the position illustrated in FIG. 1 and may be another appropriate position. The number of transmission units 20 and/or the number of reception units 30 may be any number equal to or greater than 1 depending on various conditions (or requirements) such as a heartbeat detection range and/or a heartbeat detection accuracy to be achieved by the electronic device 1.

As described later, the electronic device 1 transmits an electromagnetic wave as a transmission wave from the transmission antenna. For example, when a predetermined object (for example, a subject 200 illustrated in FIG. 1) is located around the electronic device 1, at least part of the transmission wave transmitted from the electronic device 1 is reflected off the object to become a reflected wave. For example, the reception antenna of the electronic device 1 receives such a reflected wave. In this manner, the electronic device 1 can detect the subject as a target.

The electronic device 1 including the transmission antenna may be typically a radar (Radio Detecting and Ranging) sensor that transmits and receives a radio wave. However, the electronic device 1 is not limited to a radar sensor. The electronic device 1 according to the one embodiment may be, for example, a sensor based on the LIDAR (Light Detection and Ranging, Laser Imaging Detection and Ranging) technology that uses an optical wave. Each of these sensors can include, for example, a patch antenna. Since the technologies such as the radar and the LIDAR are already known, detailed description may be appropriately simplified or omitted.

The electronic device 1 illustrated in FIG. 1 receives, from the reception antenna, the reflected wave of the transmission wave transmitted from the transmission antenna. In this manner, the electronic device 1 can detect, as a target, the predetermined subject 200 located within a predetermined distance from the electronic device 1. For example, as illustrated in FIG. 1, the electronic device 1 can measure a distance L between the electronic device 1 and the predetermined subject 200. The electronic device 1 can also measure a relative velocity between the electronic device 1 and the predetermined subject 200. The electronic device 1 can further measure a direction (an angle of arrival θ) from which the reflected wave from the predetermined subject 200 arrives at the electronic device 1.

In FIG. 1, an XY plane may be, for example, a plane substantially parallel to a ground surface. In this case, a positive Z-axis direction illustrated in FIG. 1 indicates a vertically upward direction. In FIG. 1, the electronic device 1 may be arranged on a plane parallel to the XY plane. In FIG. 1, the subject 200 may be standing on the ground surface substantially parallel to the XY plane, for example.

The subject 200 may be, for example, a person or the like located around the electronic device 1.

The subject 200 may be, for example, a living thing other than a person, such as an animal located around the electronic device 1. As described above, the subject 200 may be moving or may be stopped or stationary. In the present disclosure, objects detected by the electronic device 1 include living things such as a person, a dog, a cat, a horse, and other animals in addition to non-living things such as any object. The objects detected by the electronic device 1 in the present disclosure include a target, which includes a person, an object, and an animal, to be detected with the radar technology.

In FIG. 1, a ratio between a size of the electronic device 1 and a size of the subject 200 does not necessarily indicate an actual ratio. FIG. 1 illustrates the transmission unit 20 and the reception unit 30 installed at an outer portion of the electronic device 1. However, in one embodiment, the transmission unit 20 and/or the reception unit 30 may be installed at various positions of the electronic device 1. For example, in one embodiment, the transmission unit 20 and/or the reception unit 30 may be installed inside the electronic device 1 so as not to appear on the external appearance of the electronic device 1.

A typical example is described blow in which the transmission antenna of the electronic device 1 transmits a radio wave in a frequency band, such as a millimeter wave (equal to or higher than 30 GHz) or a quasi-millimeter wave (for example, around 20 GHz to 30 GHz). For example, the transmission antenna of the electronic device 1 may transmit a radio wave having a frequency bandwidth of 4 GHz such as from 77 GHz to 81 GHz.

Figure 2:
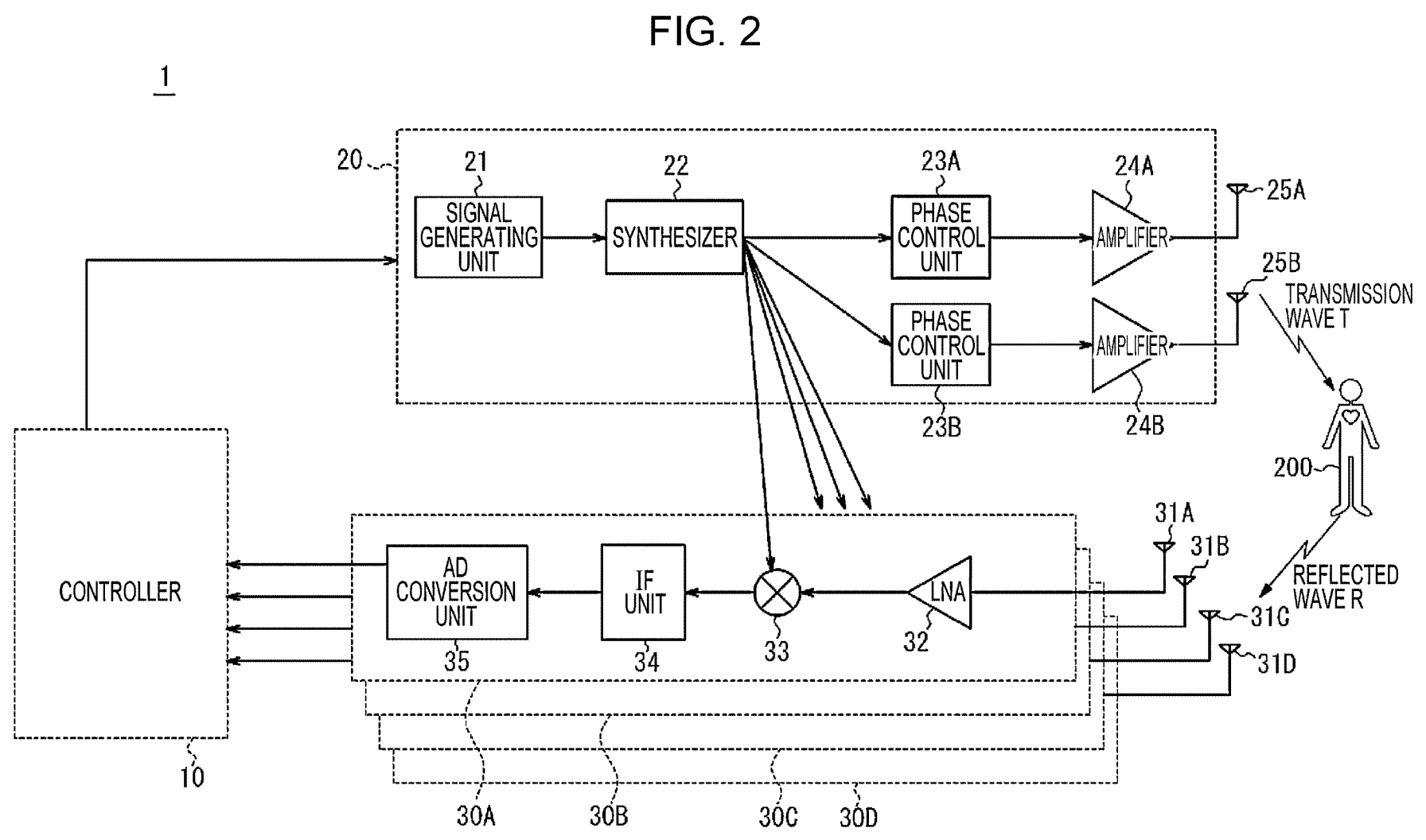
Figure 3:
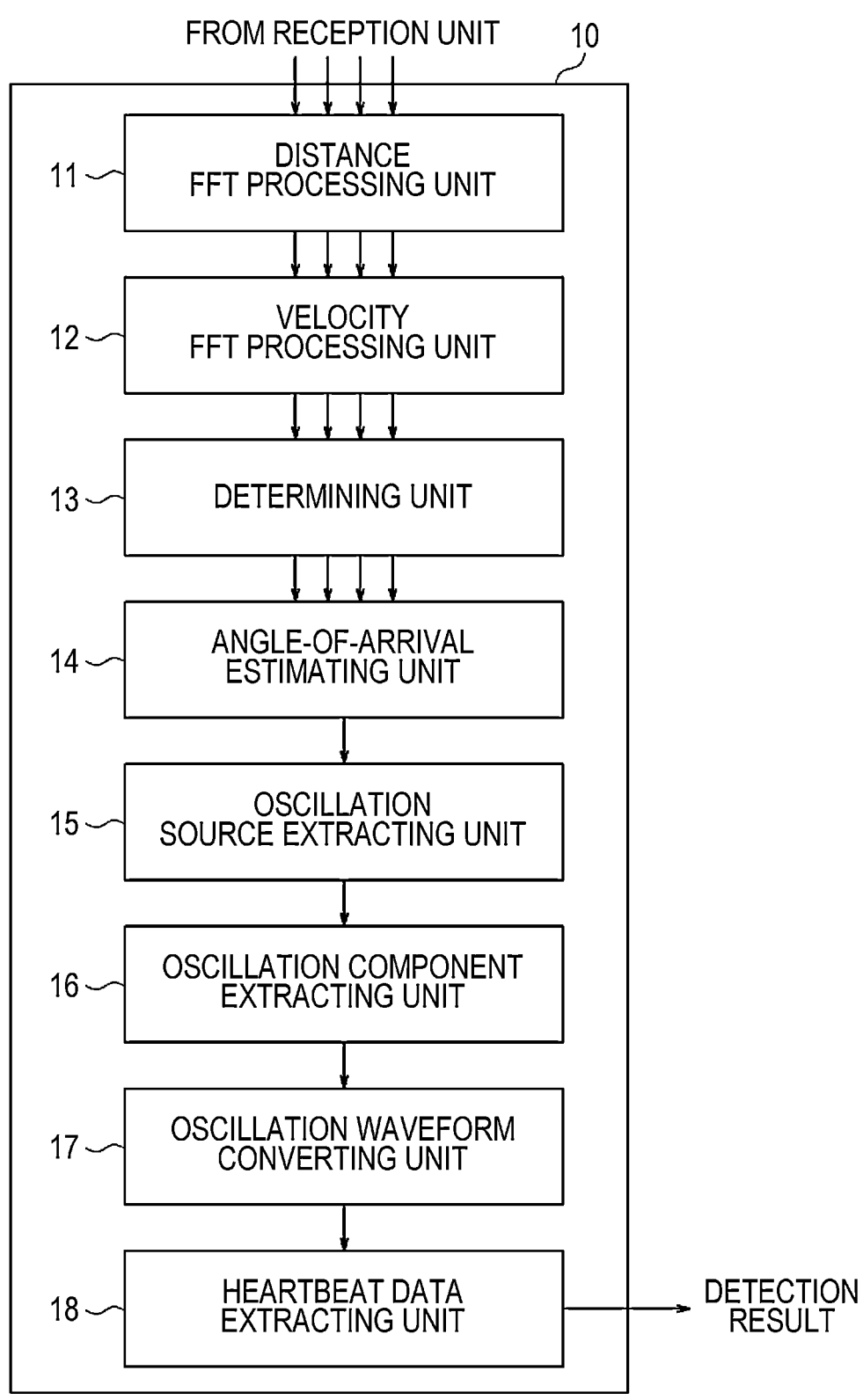
FIG. 3 is a functional block diagram illustrating part of the configuration of the electronic device according to the one embodiment.

FIG. 2 is a functional block diagram schematically illustrating an example of a configuration of the electronic device 1 according to the one embodiment. FIG. 3 is a functional block diagram illustrating in detail the controller 10 of the electronic device 1 illustrated in FIG. 2. An example of the configuration of the electronic device 1 according to the one embodiment is described below.

When a distance or the like is measured by using a millimeter-wave radar, a frequency-modulated continuous wave radar (referred to as an FMCW radar in the present disclosure) is often used. The FMCW radar sweeps a frequency of a to-be-transmitted radio wave to generate a transmission signal. Thus, a frequency of the radio wave used by such a millimeter-wave FMCW radar, which uses a radio wave of a frequency band of 79 GHz, for example, has a frequency bandwidth of 4 GHz such as from 77 GHz to 81 GHz, for example. The radar of the frequency band of 79 GHz has a feature that a usable frequency bandwidth is wider than other millimeter-wave and/or quasi-millimeter-wave radars of frequency bands of 24 GHz, 60 GHz, and 76 GHz, for example. Such an embodiment is described below as an example. The FMCW radar scheme used in the present disclosure may include an FCM scheme (Fast-Chirp Modulation) for transmitting chirp signals at a shorter period than usual. A signal generated by a signal generating unit 21 is not limited to a signal of the FM-CW scheme. The signal generated by the signal generating unit 21 may be a signal of any of various schemes other than the FM-CW scheme. A transmission signal sequence stored in any storage unit may change in accordance with these various schemes. For example, in the case of a radar signal of the FM-CW scheme described above, a signal whose frequency increases for each time sample and a signal whose frequency decreases for each time sample may be used. More detailed description of the various schemes described above is omitted because known techniques can be appropriately employed.

As illustrated in FIG. 2, the electronic device 1 according to the one embodiment includes the controller 10. The electronic device 1 according to the one embodiment may also appropriately include another functional unit such as at least any of the transmission unit 20 or reception units 30A to 30D. As illustrated in FIG. 2, the electronic device 1 may include multiple reception units such as the reception units 30A to 30D. In the present disclosure, when the reception units 30A, 30B, 30C, and 30D are not distinguished from one another, the reception units 30A, 30B, 30C, and 30D are simply referred to as "reception units 30".

As illustrated in FIG. 3, the controller 10 may include a distance FFT processing unit 11, a velocity FFT processing unit 12, a determining unit 13, an angle-of-arrival estimating unit 14, an oscillation source extracting unit 15, an oscillation component extracting unit 16, an oscillation waveform converting unit 17, and a heartbeat data extracting unit 18. These functional units included in the controller 10 are further described later.

As illustrated in FIG. 2, the transmission unit 20 may include the signal generating unit 21, a synthesizer 22, phase control units 23A and 23B, amplifiers 24A and 24B, and transmission antennas 25A and 25B. In the present disclosure, when the phase control units 23A and 23B are not distinguished from each other, the phase control units 23A and 23B are simply referred to as "phase control units 23". In the present disclosure, when the amplifiers 24A and 24B are not distinguished from each other, the amplifiers 24A and 24B are simply referred to as "amplifiers 24". In the present disclosure, when the transmission antennas 25A and 25B are not distinguished from each other, the transmission antennas 25A and 25B are simply referred to as "transmission antennas 25".

As illustrated in FIG. 2, each of the reception units 30 may include a respective one of reception antennas 31A to 31D. In the present disclosure, when the reception antennas 31A, 31B, 31C, and 31D are not distinguished from one another, the reception antennas 31A, 31B, 31C, and 31D are simply referred to as "reception antennas 31". As illustrated in FIG. 2, each of the multiple reception units 30 may include an LNA 32, a mixer 33, an IF unit 34, and an AD conversion unit 35. The reception units 30A to 30D may have the same and/or similar configuration. FIG. 2 schematically illustrates the configuration of only the reception unit 30A as a representative example.

The electronic device 1 described above may include, for example, the transmission antennas 25 and the reception antennas 31. The electronic device 1 may also appropriately include at least any of other functional units such as the controller 10.

The controller 10 included in the electronic device 1 according to the one embodiment is capable of controlling the individual functional units of the electronic device 1 and controlling operations of the entire electronic device 1. In one embodiment, the controller 10 may include a function of performing various kinds of signal processing on a reception signal received as a reflected wave by the reception unit 30. To provide control and processing capabilities for executing various functions, the controller 10 may include at least one processor, for example, a CPU (Central Processing Unit). The controller 10 may be collectively implemented by one processor, may be implemented by some processors, or may be implemented by discrete individual processors. The processor may be implemented as one integrated circuit. The integrated circuit is also referred to as an IC. The processor may be implemented as multiple integrated circuits and discrete circuits connected to be able to perform communication. The processor may be implemented based on various other known technologies. In the one embodiment, the controller 10 may be configured as, for example, a CPU and a program executed by the CPU. The controller 10 may appropriately include a memory (any storage unit) necessary for operations of the controller 10.

The any storage unit (the memory necessary for operations of the controller 10) may store a program executed by the controller 10, results of processing performed by the controller 10, and so on. The any storage unit may function as a work memory of the controller 10. The any storage unit can be implemented by a semiconductor memory or a magnetic disk, for example. However, the any storage unit is not limited to these devices, and may be implemented by any storage device. The any storage unit may be, for example, a storage medium such as a memory card inserted to the electronic device 1 according to the present embodiment. The any storage unit may be an internal memory of the CPU used as the controller 10 as described above.

In one embodiment, the any storage unit may store various parameters for setting a range in which an object is detected based on a transmission wave T transmitted from each transmission antenna 25 and a reflected wave R received from each reception antenna 31.

In the electronic device 1 according to the one embodiment, the controller 10 is capable of controlling at least one of the transmission unit 20 or the reception units 30. In this case, the controller 10 may control at least one of the transmission unit 20 or the reception units 30, based on various kinds of information stored in the any storage unit. In the electronic device 1 according to the one embodiment, the controller 10 may instruct the signal generating unit 21 to generate a signal or may control the signal generating unit 21 to generate a signal.

In one embodiment, the controller 10 may perform various kinds of signal processing on the reflected wave R received from each reception antenna 31. In one embodiment, the controller 10 may perform various kinds of signal processing on the transmission wave T transmitted from each transmission antenna 25 and/or the reflected wave R received from each reception antenna 31. In one embodiment, the controller 10 may implement at least some of functions of at least one of the transmission unit 20 or the reception units 30.

In accordance with control performed by the controller 10, the signal generating unit 21 generates a signal (transmission signal) to be transmitted as the transmission wave T from each of the transmission antennas 25. When generating a transmission signal, the signal generating unit 21 may allocate a frequency of the transmission signal in accordance with control performed by the controller 10, for example. Specifically, the signal generating unit 21 may allocate the frequency of the transmission signal in accordance with a parameter set by the controller 10, for example. For example, the signal generating unit 21 receives frequency information from the controller 10 or the any storage unit and generates a signal having a predetermined frequency in a frequency band such as from 77 GHz to 81 GHz, for example. The signal generating unit 21 may include a functional unit such as a voltage control oscillator (VCO), for example.

The signal generating unit 21 may be configured as hardware having the function, for example as a microcomputer, or for example as a processor such as a CPU and a program or the like executed by the processor. Each functional unit described below may also be configured as hardware having the function, for example as a microcomputer if possible, or for example as a processor such as a CPU and a program or the like executed by the processor if possible.

In the electronic device 1 according to the one embodiment, the signal generating unit 21 may generate a transmission signal (transmission chirp signal) such as a chirp signal, for example. In particular, the signal generating unit 21 may generate a signal (linear chirp signal) whose frequency changes linearly and periodically. For example, the signal generating unit 21 may generate a chirp signal whose frequency linearly and periodically increases from 77 GHz to 81 GHz as time elapses. For example, the signal generating unit 21 may generate a signal whose frequency periodically repeats a linear increase (up-chirp) from 77 GHz to 81 GHz and a decrease (down-chirp) as time elapses. For example, the controller 10 may set in advance the signal generated by the signal generating unit 21. For example, the any storage unit or the like may store in advance the signal generated by the signal generating unit 21. Since a chirp signal used in a technical field such as the radar is known, more detailed description is appropriately simplified or omitted. The signal generated by the signal generating unit 21 is supplied to the synthesizer 22.

Figure 4:
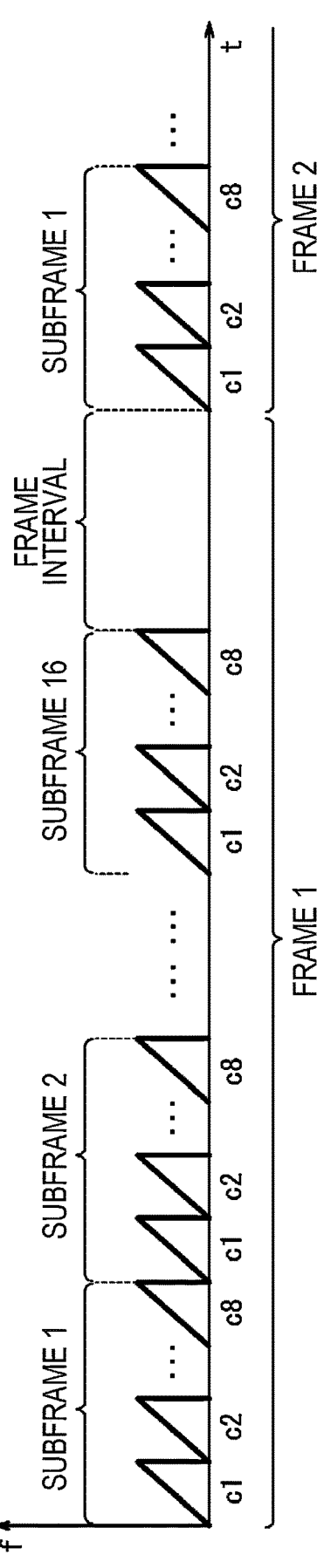
FIG. 4 is a diagram for describing a configuration of a transmission signal according to the one embodiment.

FIG. 4 is a diagram for describing an example of chirp signals generated by the signal generating unit 21.

In FIG. 4, the horizontal axis represents elapsed time and the vertical axis represents a frequency. In the example illustrated in FIG. 4, the signal generating unit 21 generates linear chirp signals whose frequency changes linearly and periodically. FIG. 4 illustrates chirp signals c1, c2, . . . , c8. As illustrated in FIG. 4, the frequency of each chirp signal linearly increases as time elapses.

In the example illustrated in FIG. 4, one subframe includes eight chirp signals c1, c2, . . . , c8. That is, each of subframes such as a subframe 1 and a subframe 2 illustrated in FIG. 4 includes eight chirp signals c1, c2, . . . , c8. In the example illustrated in FIG. 4, one frame includes 16 subframes such as the subframes 1 to 16. That is, each of frames such as a frame 1 and a frame 2 illustrated in FIG. 4 includes 16 subframes. As illustrated in FIG. 4, a frame interval of a predetermined length may be included between frames. One frame illustrated in FIG. 4 may have a length of about 30 ms to 50 ms, for example.

In FIG. 4, the frame 2 and subsequent frames may have the same and/or similar configuration. In FIG. 4, the frame 3 and subsequent frames may have the same and/or similar configuration. In the electronic device 1 according to the one embodiment, the signal generating unit 21 may generate a transmission signal as any number of frames. In FIG. 4, an illustration of some chirp signals is omitted. As described above, for example, the any storage unit or the like may store a relationship between time and a frequency of the transmission signal generated by the signal generating unit 21.

As described above, the electronic device 1 according to the one embodiment may transmit a transmission signal made up of subframes each including multiple chirp signals. The electronic device 1 according to the one embodiment may transmit a transmission signal made up of frames each including a predetermined number of subframes.

In the description below, the electronic device 1 transmits a transmission signal having a frame structure illustrated in FIG. 4. However, the frame structure illustrated in FIG. 4 is an example. For example, the number of chirp signals included in one subframe is not limited to eight. In one embodiment, the signal generating unit 21 may generate a subframe including any number of (for example, multiple) chirp signals. The subframe structure illustrated in FIG. 4 is also an example. For example, the number of subframes included in one frame is not limited to 16. In one embodiment, the signal generating unit 21 may generate a frame including any number of (for example, multiple) subframes. The signal generating unit 21 may generate signals having different frequencies. The signal generating unit 21 may generate multiple discrete signals of bandwidths in which frequencies f are different from each other.

Referring back to FIG. 2, the synthesizer 22 increases the frequency of the signal generated by the signal generating unit 21 to a frequency in a predetermined frequency band. The synthesizer 22 may increase the frequency of the signal generated by the signal generating unit 21 to a frequency selected as a frequency of the transmission wave T to be transmitted from each of the transmission antennas 25. For example, the controller 10 may set the frequency selected as the frequency of the transmission wave T to be transmitted from each of the transmission antennas 25. For example, the any storage unit may store the frequency selected as the frequency of the transmission wave T to be transmitted from each of the transmission antennas 25. The signal whose frequency has been increased by the synthesizer 22 is supplied to the phase control unit 23 and the mixer 33. When the multiple phase control units 23 are present, the signal whose frequency has been increased by the synthesizer 22 may be supplied to each of the multiple phase control units 23. When the multiple reception units 30 are present, the signal whose frequency has been increased by the synthesizer 22 may be supplied to the mixer 33 of each of the multiple reception units 30.

Each of the phase control units 23 controls a phase of the transmission signal supplied from the synthesizer 22. Specifically, for example, in accordance with control performed by the controller 10, each of the phase control units 23 may appropriately advance or delay the phase of the signal supplied from the synthesizer 22 to adjust the phase of the transmission signal. In this case, based on a difference between paths of the respective transmission waves T to be transmitted from the multiple transmission antennas 25, the phase control units 23 may adjust the phases of the respective transmission signals. The phase control units 23 appropriately adjust the phases of the respective transmission signals, so that the transmission waves T transmitted from the multiple transmission antennas 25 enhance with each other in a predetermined direction to form a beam (beamforming). In this case, for example, the any storage unit may store a correlation between a direction of beamforming and amounts of phase by which the respective transmission signals transmitted by the multiple transmission antennas 25 are to be controlled. The transmission signal whose phase is controlled by each of the phase control units 23 is supplied to a respective one of the amplifiers 24.

The amplifier 24 amplifies power (electric power) of the transmission signal supplied from the phase control unit 23 in accordance with control performed by the controller 10, for example. When the electronic device 1 includes the multiple transmission antennas 25, each of the multiple amplifiers 24 may amplify power (electric power) of the transmission signal supplied from a respective one of the multiple phase control units 23 in accordance with control performed by the controller 10, for example. Since the technology for amplifying power of a transmission signal is already known, more detailed description is omitted. The amplifier 24 is connected to the transmission antenna 25.

The transmission antenna 25 outputs (transmits), as the transmission wave T, the transmission signal amplified by the amplifier 24. When the electronic device 1 includes the multiple transmission antennas 25, each of the multiple transmission antennas 25 may output (transmit), as the transmission wave T, the transmission signal amplified by a respective one of the multiple amplifiers 24. Since the transmission antennas 25 can have a configuration that is the same as and/or similar to the configuration of transmission antennas for use in the known radar technology, more detailed description is omitted.

Accordingly, the electronic device 1 according to the one embodiment, which includes the transmission antennas 25, can transmit transmission signals (for example, transmission chirp signals) as the transmission waves T from the respective transmission antennas 25. At least one of the functional units of the electronic device 1 may be housed in one housing. In this case, the one housing may have a hard-to-open structure. For example, the transmission antennas 25, the reception antennas 31, and the amplifiers 24 are desirably housed in one housing, and this housing desirably has a hard-to-open structure. When the electronic device 1 is installed on a stationary object, each of the transmission antennas 25 may transmit the transmission wave T to outside the stationary object through a cover member such as a radar cover, for example. In this case, the radar cover may be made of a material, for example, a synthetic resin or rubber, that allows an electromagnetic wave to pass therethrough. This radar cover may also serve as a housing of the electronic device 1, for example. Covering the transmission antennas 25 with a member such as the radar cover can reduce a risk of the transmission antennas 25 being damaged or malfunctioning because of a contact with an external object. The radar cover and the housing may also be referred to as a radome.

FIG. 2 illustrates an example of the electronic device 1 that includes two transmission antennas 25. However, in one embodiment, the electronic device 1 may include any number of transmission antennas 25. On the other hand, in one embodiment, the electronic device 1 may include the multiple transmission antennas 25 when the transmission waves T transmitted from the respective transmission antennas 25 form a beam in a predetermined direction. In one embodiment, the electronic device 1 may include multiple transmission antennas 25. In this case, the electronic device 1 may include the multiple phase control units 23 and the multiple amplifiers 24 to correspond to the multiple transmission antennas 25. Each of the multiple phase control units 23 may control the phase of a respective one of the multiple transmission waves supplied from the synthesizer 22 and to be transmitted from the respective transmission antennas 25. Each of the multiple amplifiers 24 may amplify power of a respective one of the multiple transmission signals to be transmitted from the respective transmission antennas 25. In this case, the electronic device 1 may include the multiple transmission antennas. As described above, when the electronic device 1 illustrated FIG. 2 includes the multiple transmission antennas 25, the electronic device 1 may include multiple functional units necessary for transmitting the transmission waves T from the multiple transmission antennas 25.

The reception antenna 31 receives the reflected wave R. The reflected wave R may be the transmission wave T reflected off the predetermined subject 200. As the reception antenna 31, multiple antennas such as the reception antennas 31A to 31D, for example, may be included. Since the reception antennas 31 can have a configuration that is the same as and/or similar to the configuration of reception antennas for use in the known radar technology, more detailed description is omitted. The reception antenna 31 is connected to the LNA 32. A reception signal based on the reflected wave R received by the reception antenna 31 is supplied to the LNA 32.

The electronic device 1 according to the one embodiment can receive, from each of the multiple reception antennas 31, the reflected wave R that is the transmission wave T that has been transmitted as the transmission signal (transmission chirp signal) such as a chirp signal, for example, and has been reflected off the predetermined subject 200. When the transmission chirp signal is transmitted as the transmission wave T in this manner, the reception signal based on the received reflected wave R is referred to as a reception chirp signal. That is, the electronic device 1 receives the reception signal (for example, the reception chirp signal) as the reflected wave R from each of the reception antennas 31. When the electronic device 1 is installed on a stationary object, each of the reception antennas 31 may receive the reflected wave R from the outside of the stationary object through a cover member such as a radar cover, for example. In this case, the radar cover may be made of a material, for example, a synthetic resin or rubber, that allows an electromagnetic wave to pass therethrough. This radar cover may also serve as a housing of the electronic device 1, for example. Covering the reception antennas 31 with a member such as the radar cover can reduce a risk of the reception antennas 31 being damaged or malfunctioning because of a contact with an external object. The radar cover and the housing may also be referred to as a radome.

When the reception antenna 31 is installed near the transmission antenna 25, these reception antenna 31 and transmission antenna 25 may be collectively included in the one electronic device 1. That is, for example, the one electronic device 1 may include at least one transmission antenna 25 and at least one reception antenna 31. For example, the one electronic device 1 may include multiple transmission antennas 25 and multiple reception antennas 31. In such a case, one radar sensor may be covered with a cover member such as one radar cover, for example.

The LNA 32 amplifies, with low noise, the reception signal based on the reflected wave R received by the reception antenna 31. The LNA 32 may be a low-noise amplifier and amplifies, with low noise, the reception signal supplied from the reception antenna 31. The reception signal amplified by the LNA 32 is supplied to the mixer 33.

The mixer 33 mixes (multiplies) the reception signal having a radio frequency (RF) and supplied from the LNA 32 and the transmission signal supplied from the synthesizer 22 to generate a beat signal. The beat signal obtained by the mixer 33 through mixing is supplied to the IF unit 34.

The IF unit 34 performs frequency conversion on the beat signal supplied from the mixer 33 to decrease the frequency of the beat signal to an intermediate frequency (IF). The beat signal whose frequency has been decreased by the IF unit 34 is supplied to the AD conversion unit 35.

The AD conversion unit 35 digitizes the analog beat signal supplied from the IF unit 34. The AD conversion unit 35 may be configured as any analog-to-digital conversion circuit (Analog-to-Digital Converter (ADC)). The digitized beat signal obtained by the AD conversion unit 35 is supplied to the distance FFT processing unit 11 of the controller 10. When the multiple reception units 30 are present, the digitized beat signals obtained by the respective AD conversion units 35 may be supplied to the distance FFT processing unit 11.

The distance FFT processing unit 11 of the controller 10 illustrated in FIG. 3 performs processing for estimating a distance between the electronic device 1 and the subject 200, based on the beat signals supplied from the AD conversion units 35 of the reception units 30. The distance FFT processing unit 11 may include a processing unit that performs fast Fourier transform, for example. In this case, the distance FFT processing unit 11 may be configured as any circuit, any chip, or the like that performs fast Fourier transform (FFT). The distance FFT processing unit 11 may preform Fourier transform other than fast Fourier transform.

The distance FFT processing unit 11 performs FFT processing (appropriately referred to as "distance FFT processing" in the present disclosure) on the digitized beat signals obtained by the AD conversion units 35. For example, the distance FFT processing unit 11 may perform FFT processing on complex signals supplied from the AD conversion units 35. The digitized beat signals obtained by the AD conversion units 35 can be represented as temporal changes in signal intensity (power). The distance FFT processing unit 11 performs FFT processing on such beat signals, so that the beat signals can be represented as a signal intensity (power) for each frequency. Through the distance FFT processing performed by the distance FFT processing unit 11, complex signals corresponding to the distance can be obtained based on the digitized beat signals obtained by the AD conversion units 35.

If a peak in a result obtained by the distance FFT processing is equal to or greater than a predetermined threshold, the distance FFT processing unit 11 may determine that the predetermined subject 200 is located at the distance corresponding to the peak. For example, a method is known in which an object (reflecting object) that reflects a transmission wave is determined to be present if a peak value that is equal to or greater than a threshold is detected from the average power or amplitude of a disturbance signal as in constant false alarm rate (CFAR)-based detection processing.

As described above, the electronic device 1 according to the one embodiment can detect, as the target, the subject 200 that reflects the transmission wave T, based on the transmission signal transmitted as the transmission wave T and the reception signal received as the reflected wave R. In one embodiment, for example, the controller 10 of the electronic device 1 may perform the operation described above.

The distance FFT processing unit 11 can estimate a distance to a predetermined object, based on one chirp signal (for example, c1 illustrated in FIG. 3). That is, the electronic device 1 can measure (estimate) the distance L illustrated in FIG. 1 by performing the distance FFT processing. Since a technique for measuring (estimating) a distance to a predetermined object by performing FFT processing on a beat signal is known, more detailed description is appropriately simplified or omitted. The result (for example, distance information) of the distance FFT processing performed by the distance FFT processing unit 11 may be supplied to the velocity FFT processing unit 12. The result of the distance FFT processing performed by the distance FFT processing unit 11 may also be supplied to the determining unit 13, the angle-of-arrival estimating unit 14, the oscillation source extracting unit 15, and/or the like at the subsequent stage.

The velocity FFT processing unit 12 performs processing for estimating a relative velocity between the electronic device 1 and the subject 200, based on the beat signals on which the distance FFT processing unit 11 has performed the distance FFT processing. The velocity FFT processing unit 12 may include a processing unit that performs fast Fourier transform, for example. In this case, the velocity FFT processing unit 12 may be configured as any circuit, any chip, or the like that performs fast Fourier transform (FFT). The velocity FFT processing unit 12 may preform Fourier transform other than fast Fourier transform.

The velocity FFT processing unit 12 further performs FFT processing (appropriately referred to as "velocity FFT processing" in the present disclosure) on the beat signals on which the distance FFT processing unit 11 has performed the distance FFT processing. For example, the velocity FFT processing unit 12 may perform FFT processing on the complex signals supplied from the distance FFT processing unit 11. The velocity FFT processing unit 12 can estimate a relative velocity of the predetermined object, based on a subframe (for example, the subframe 1 illustrated in FIG. 3) including chirp signals. Through the velocity FFT processing performed on the multiple chirp signals by the velocity FFT processing unit 12, complex signals corresponding to the relative velocity can be obtained based on the complex signals corresponding to the distance obtained by the distance FFT processing unit 11.

When the distance FFT processing is performed on the beat signal in the above-described manner, multiple vectors can be generated. The velocity FFT processing unit 12 can estimate a relative velocity of the predetermined object by determining a phase of a peak in a result of the velocity FFT processing performed on these multiple vectors. That is, the electronic device 1 can measure (estimate) a relative velocity between the electronic device 1 and the predetermined subject 200 illustrated in FIG. 1 by performing the velocity FFT processing. Since a technique for measuring (estimating) a relative velocity of a predetermined object by performing velocity FFT processing on a result of distance FFT processing is known, more detailed description is appropriately simplified or omitted. The result (for example, velocity information) of the velocity FFT processing performed by the velocity FFT processing unit 12 may be supplied to the determining unit 13. The result of the velocity FFT processing performed by the velocity FFT processing unit 12 may also be supplied to the angle-of-arrival estimating unit 14, the oscillation source extracting unit 15, and/or the like at the subsequent stage.

When performing velocity FFT processing, the velocity FFT processing unit 12 may apply window control to avoid the occurrence of discontinuities. In such a case, the velocity FFT processing unit 12 may skip outputting a relative velocity adjacent to the relative velocity of the stationary object.

The determining unit 13 performs determination processing for a distance and/or a relative velocity, based on the result of the distance FFT processing performed by the distance FFT processing unit 11 and/or the result of the velocity FFT processing performed by the velocity FFT processing unit 12. The determining unit 13 determines whether an object is detected at a predetermined distance and/or a predetermined relative velocity. The determination performed by the determining unit 13 is further described below.

In a common FM-CW radar technology, whether a target is present can be determined based on a result of fast Fourier transform processing or the like performed on a beat frequency extracted from a reception signal. The result of the fast Fourier transform processing or the like performed on the beat frequency extracted from the reception signal includes a noise component due to clutter (extraneous reflection component) or the like. Thus, processing for removing the noise component from the processing result of the reception signal and extracting a target signal alone may be performed.

Methods for determining whether the target is present include a scheme (threshold detection scheme) in which a threshold is set for the output of the reception signal and the target is determined to be present if the intensity of the reflected signal exceeds the threshold. When this scheme is employed, the target is also determined if the signal intensity of clutter exceeds the threshold. Consequently, a so-called "false alarm" is issued. Whether this signal intensity of clutter exceeds the threshold is a matter of a probability. The probability of this signal intensity of clutter exceeding the threshold is called "a probability of false alarm". As a method for suppressing this probability of false alarm to be low and constant, the constant false alarm rate can be used.

In the present disclosure, the constant false alarm rate is simply referred to also as CFAR. CFAR employs an assumption that the signal intensity (amplitude) of noise conforms to a Rayleigh distribution. Based on this assumption, when a weight for calculating a threshold for use in determining whether a target is detected is fixed, an error rate of target detection becomes theoretically constant regardless of the amplitude of noise.

A scheme called Cell-Averaging CFAR (also referred to as CA-CFAR in the present disclosure) is known CFAR in the common radar technology. In CA-CFAR, a signal intensity value (for example, an amplitude value) of the reception signal having undergone predetermined processing may be sequentially input to a shift register at a constant sampling frequency. This shift register includes a cell under test at the center thereof and includes multiple reference cells on both sides of the cell under test. Every time the signal intensity value is input to the shift register, each signal intensity value input previously is moved from a cell on one end side (for example, a left end side) to a cell on the other end side (for example, a right end side) of the shift register by one. In synchronization with the input timing, the values in the reference cells are averaged. The average value thus obtained is multiplied by a prescribed weight, and the result is calculated as a threshold. If the value in the cell under test is greater than the threshold thus calculated, the value in the cell under test is output. On the other hand, if the value in the cell under test is not greater than the calculated threshold, a value of 0 (zero) is output. As described above, in CA-CFAR, the threshold is calculated from the average value of the values in the reference cells and whether a target is present is determined. In this manner, a detection result can be obtained.

In CA-CFAR, for example, when multiple targets are present in the vicinity to each other, the threshold calculated in the vicinity of the targets increases because of the nature of the algorithm. Thus, there may be a target that is not detected regardless of the sufficient signal intensity. Likewise, when there is a clutter step, the calculated threshold increases also in the vicinity of the clutter step. In this case, detection of a small target located in the vicinity of the clutter step may fail.

In relation to CA-CFAR described above, there is a technique called Order Statistic CFAR (also referred to as OS-CFAR in the present disclosure) as a technique for obtaining a threshold from the median (median value) of the values in the reference cells or from a value at a prescribed place in order of the values in the reference cells sorted in ascending order. OS-CFER is a technique in which a threshold is set based on ordered statistics and a target is determined to be present if the signal intensity exceeds the threshold. This OS-CFAR can deal with the above-described issues in CA-CFAR. OS-CFAR can be implemented by performing processing that is partially different from the processing of CA-CFAR. In the description below, the electronic device 1 according to the one embodiment performs the OS-CFAR processing.

The determining unit 13 may use OS-CFAR to determine whether an object is detected. In this case, the determining unit 13 may use different thresholds for an area of a stationary object and an area of a non-stationary object to perform the determination. The determining unit 13 may skip detecting an area of the relative velocity adjacent to that of the stationary object when the above-described window control is performed. The determining unit 13 may use an area of a different distance at the same relative velocity, as an area of noise used in OS-CFAR.

The angle-of-arrival estimating unit 14 estimates a direction (angle of arrival) from which the reflected wave R arrives from the predetermined subject 200, based on a result of the determination performed by the determining unit 13. The angle-of-arrival estimating unit 14 may estimate the angle of arrival for a point for which the determining unit 13 has determined that the threshold is satisfied. The electronic device 1 can estimate the direction from which the reflected wave R arrives, by receiving the reflected wave R from the multiple reception antennas 31. For example, the multiple reception antennas 31 are arranged at a predetermined interval. In this case, the transmission wave T transmitted from the transmission antenna 25 is reflected off the predetermined subject 200 to become the reflected wave R. Each of the multiple reception antennas 31 arranged at the predetermined interval receives the reflected wave R. The angle-of-arrival estimating unit 14 can estimate the direction from which the reflected wave R arrives at each of the multiple reception antennas 31, based on the phases of the respective reflected waves R received by the multiple reception antennas 31 and a difference between paths of the respective reflected waves R. That is, the electronic device 1 can measure (estimate) the angle of arrival θ illustrated in FIG. 1, based on the result of the velocity FFT processing.

Various techniques for estimating the direction from which the reflected wave R arrives based on a result of velocity FFT processing have been proposed. For example, MUSIC (MUltiple SIgnal Classification), ESPRIT (Estimation of Signal Parameters via Rotational Invariance Technique), and the like are known direction-of-arrival estimation algorithms. Thus, more detailed description of the known techniques is appropriately simplified or omitted. Information (angle information) of the angle of arrival θ estimated by the angle-of-arrival estimating unit 14 may be appropriately supplied to the oscillation source extracting unit 15 and/or the like in the controller 10.

As described above, in the one embodiment, the controller 10 can detect an object located in a range in which the transmission waves T are transmitted, based on the information supplied from at least any of the distance FFT processing unit 11, the velocity FFT processing unit 12, or the angle-of-arrival estimating unit 14. The controller 10 may perform detection of an object by performing, for example, clustering processing based on the supplied distance information, velocity information, and angle information. For example, DBSCAN (Density-based spatial clustering of applications with noise) or the like is a known algorithm used in clustering of data. In the clustering processing, for example, average power of points constituting the detected object may be calculated. The distance information, the velocity information, the angle information, and the power information of the object detected by the controller 10 may be supplied to another device, for example. The controller 10 may calculate the average power of the point cloud representing the object.

The oscillation source extracting unit 15 extracts an oscillation source including a body movement such as a heartbeat in a human body, based on the information input to the oscillation source extracting unit 15. The oscillation source extracting unit 15 may extract the oscillation source including a body movement such as a heartbeat in a human body, based on various algorithms. For example, the reflected wave R received from the reception antenna 31 includes Doppler shift corresponding to a relative velocity to the subject 200. If the subject 200 is a person, the Doppler shift changes over time. Thus, the oscillation source can be determined to be a body movement of the person. On the other hand, if the subject 200 is not a person but is a machine, for example, the Doppler shift does not change over time and takes a constant value. Thus, the oscillation source can be determined not to be a body movement of a person. Information of the oscillation source extracted by the oscillation source extracting unit 15 may be supplied to, for example, the oscillation component extracting unit 16 and/or the like.

Figure 5:
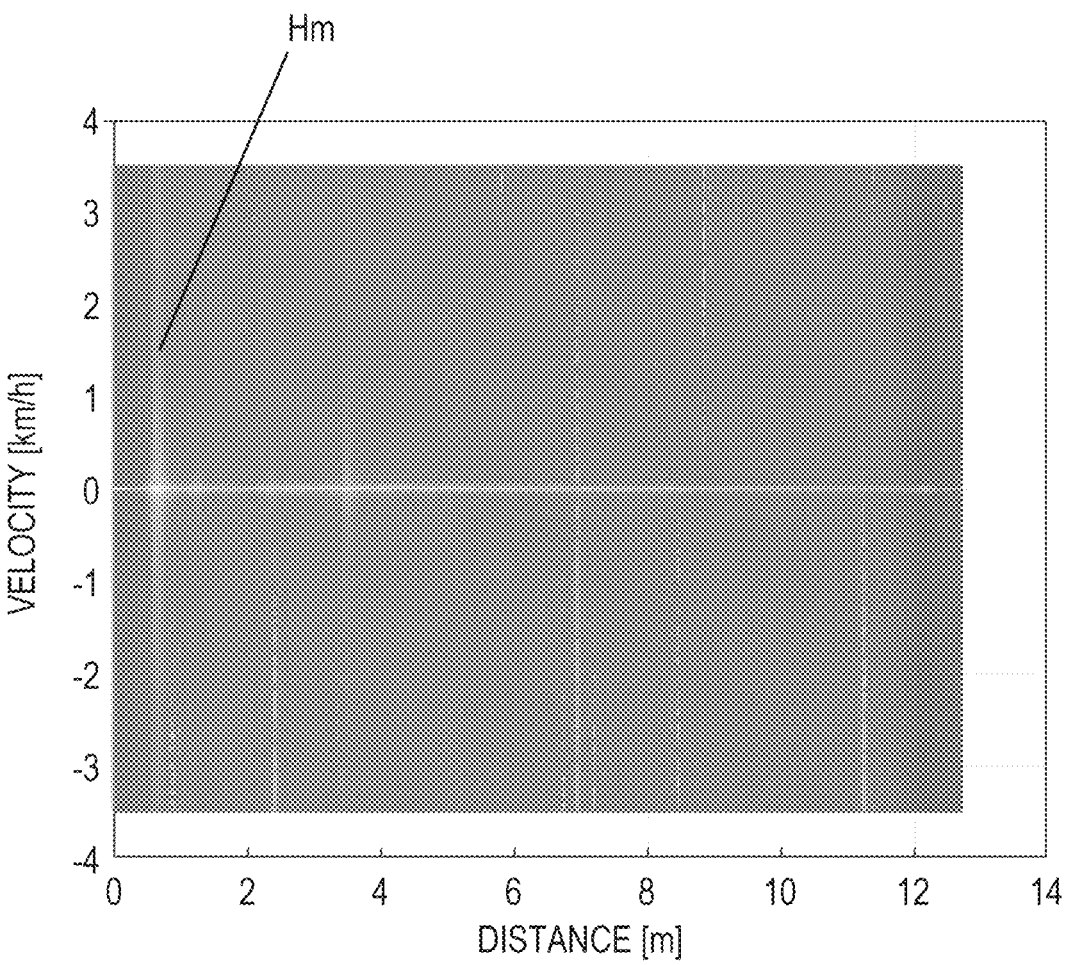
FIG. 5 is a flowchart for describing an operation of the electronic device according to the one embodiment.

For example, the oscillation source extracting unit 15 may determine that an oscillation source including a body movement such as a heartbeat in a human body is located at a distance over a predetermined velocity range or greater in an oscillation spectrum as illustrated in FIG. 5 and extract the oscillation source. FIG. 5 is a graph illustrating a result of two-dimensional fast Fourier transform (2D FFT). In FIG. 5, the horizontal axis represents a distance (range) and the vertical axis represents a velocity. The oscillation source extracting unit 15 may extract, for example, a peak Hm illustrated in FIG. 5, as an oscillation source including a body movement such as a heartbeat in a human body.

Figure 6:
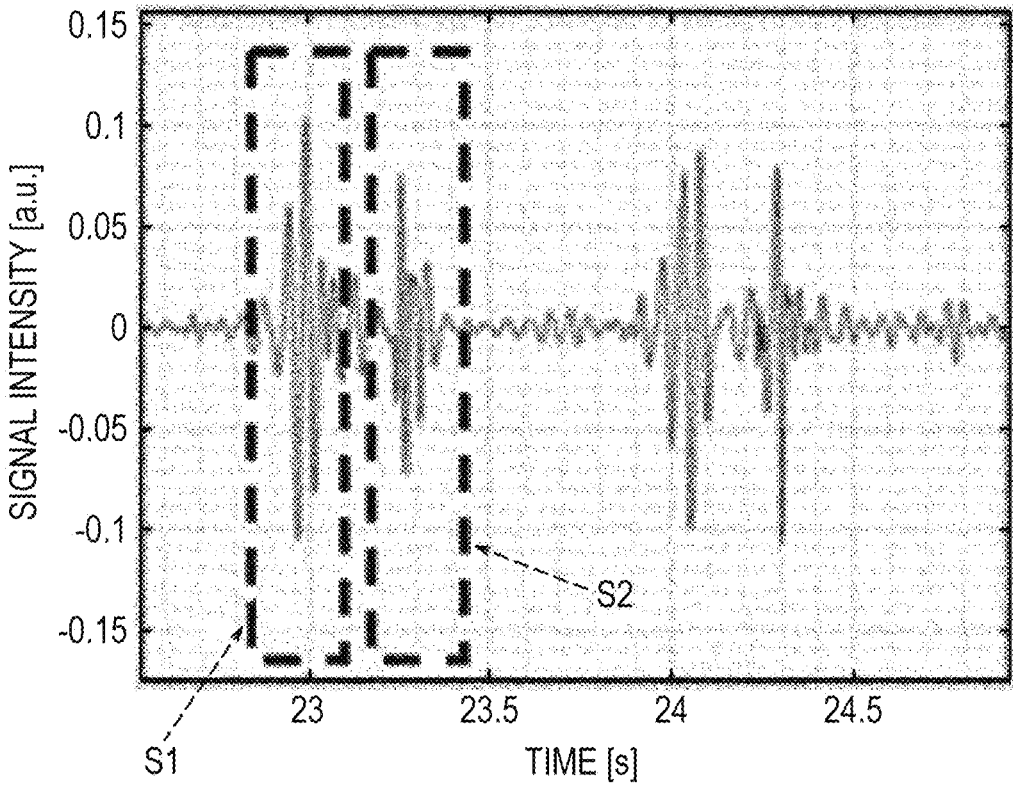
FIG. 6 is a diagram illustrating an example of processing performed in a controller according to the one embodiment.

The oscillation source extracting unit 15 may extract an oscillation source including a body movement such as a heartbeat in a human body, for example, by using a frequency filter and/or time-space-frequency decomposition. For example, the oscillation source extracting unit 15 may extract heart sounds (for example, a first heart sound S1 and a second heart sound S2) illustrated in FIG. 6. The oscillation source extracting unit 15 may extract, for example, envelopes of heart sounds such as the first heart sound S1 and the second heart sound S2. In FIG. 6, the horizontal axis represents time and the vertical axis represents signal intensity.

In FIG. 5 illustrating an example of the 2D FFT calculation result, Hm denotes a dispersion of the Doppler shift caused by a body movement of a person. In FIG. 6, a long line extending in the vertical direction is a bright line. By detecting this bright line, the oscillation source extracting unit 15 extracts an oscillation source including a body movement such as a heartbeat in a human body, based on the information input to the oscillation source extracting unit 15 as described above. The oscillation source extracting unit 15 may extract the oscillation source including a body movement such as a heartbeat in a human body, based on various algorithms.

Detection of a bright line is further described. In one embodiment, detection of a bright line may be performed, for example, based on steps described below.

Step 1: Let F(i, j) denote an absolute value of a result (point cloud) of performing CFAR on the 2D FFT calculation result. For a certain threshold Fth, a point could that satisfies F(i, j)>=Fth is extracted, and the result is denoted by F'(i, j). F'(i, j) denotes a point cloud.

Step 2: Grouping is performed on the point cloud F'(i, j) by using DBSCAN or the like. Let Gk denote a k-th group among the groups, and let Tk denote a vertical width of the group (vertical width of the bright line).

Step 3: A threshold Tth is set for the vertical width of the Doppler shift. k for which Tk>Tth is satisfied is searched for, so that a distance (range) at which Gk is located is determined to be a distance (range) at which a person is present.

The oscillation source extracting unit 15 may extract a heart rate or a heartbeat interval based on oscillation of the oscillation source in the following manner. That is, for example, the oscillation source extracting unit 15 extracts the first heart sound S1 and the second heart sound S2 as illustrated in FIG. 6. In this case, the oscillation source extracting unit 15 may calculate a heartbeat interval or a heart rate (the number of heartbeats for one minutes), based on an interval between a center time of the first heart sound S1 and a center time of the next first heart sound S1 or an interval between a peak of an envelope of the first heart sound S1 and a peak of an envelope of the next first heart sound S1.

The oscillation component extracting unit 16 extracts an oscillation component including a body movement such as a heartbeat in a human body, based on the information of the oscillation source extracted by the oscillation source extracting unit 15. Information of the oscillation component extracted by the oscillation component extracting unit 16 may be supplied to, for example, the oscillation waveform converting unit 17.

In one embodiment, the oscillation component extracting unit 16 may extract a component of the oscillation source, for example, based on steps described below.

Step 1: The oscillation component extracting unit 16 extracts only information of the oscillation source from the 2D FFT result. A technique of extracting only information of the oscillation source to be used may be, for example, a technique such as the above-described oscillation source extraction method performed by the oscillation source extracting unit 15, a method of determining that the oscillation source including a body movement such as a heartbeat in a human body is located at a distance over a predetermined velocity range or greater and extracting the oscillation source, or a method of extracting the peak Hm illustrated in FIG. 5 as the oscillation source including a body movement such as a heartbeat in a human body. After extracting only the information of the oscillation source, the oscillation component extracting unit 16 performs inverse FFT or the like on the result to generate a time-series oscillation waveform.

Step 2: The oscillation component extracting unit 16 performs frequency selection on the generated time-series oscillation waveform by using a frequency filter and/or a discrete/continuous wavelet transform to extract an intended oscillation component.

The oscillation waveform converting unit 17 converts the oscillation waveform, based on the oscillation component extracted by the oscillation component extracting unit 16. Information of the converted oscillation waveform obtained by the oscillation waveform converting unit 17 may be supplied to, for example, the heartbeat data extracting unit 18.

In one embodiment, the oscillation waveform converting unit 17 may use, for example, transform processing represented by Expression (1) below to convert the Doppler shift φ into an oscillation velocity.

$$v = c * f * \arg(\varphi)/(4\pi * Ts) \tag{1}$$

Note that in Expression (1) above, v denotes an oscillation velocity, c denotes a light velocity, f denotes a center frequency of a chirp, and Ts denotes a time between chirps.

The heartbeat data extracting unit 18 extracts heartbeat data of the human body, based on a result of information processing performed up to the previous stage. The heartbeat data of the subject 200 extracted by the heartbeat data extracting unit 18 may be output from the controller 10 as a detection result of the heartbeat of the subject 200 who is a person, for example.

The electronic device 1 illustrated in FIG. 2 includes the two transmission antennas 25 and the four reception antennas 31. However, the electronic device 1 according to the one embodiment may include any number of transmission antennas 25 and any number of reception antennas 31. For example, since the electronic device 1 includes the two transmission antennas 25 and the four reception antennas 31, the electronic device 1 can be considered to include a virtual antenna array virtually including eight antennas. As described above, the electronic device 1 may receive the reflected wave R of 16 subframes illustrated in FIG. 4 by using, for example, the eight virtual antennas.

An operation of the electronic device 1 according to the one embodiment is described.

Figure 7:
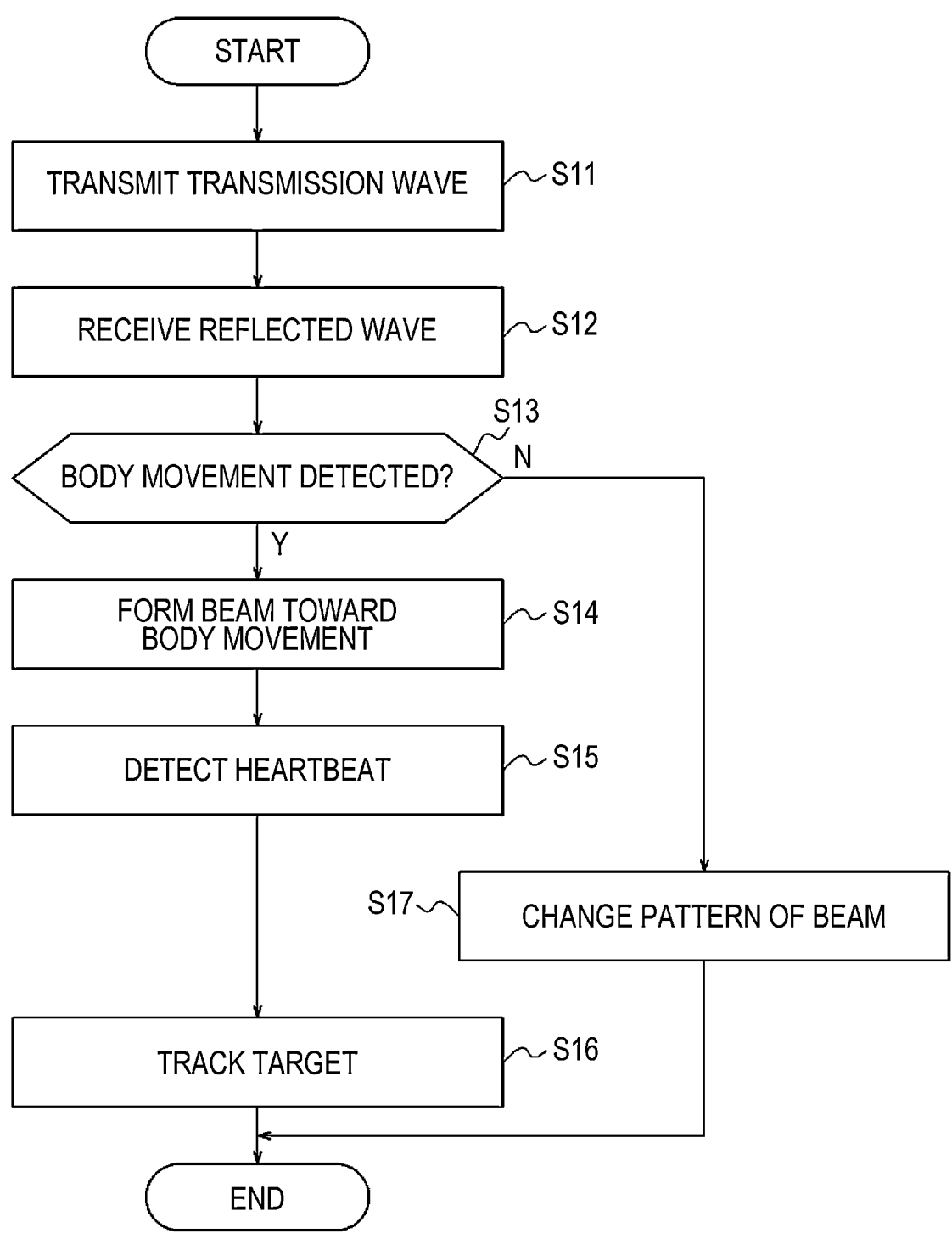
FIG. 7 is a diagram illustrating an example of processing performed in the controller according to the one embodiment.

FIG. 7 is a flowchart for describing an operation performed by the electronic device 1. A flow of the operation performed by the electronic device 1 is briefly described below. For example, the electronic device 1 may start the operation illustrated in FIG. 5 when detecting a heartbeat of a person located around the electronic device 1.

After the process illustrated FIG. 5 is started, the controller 10 performs control so that a transmission wave is transmitted from the transmission antenna 25 of the electronic device 1 (step S11). In step S11, the controller 10 may perform control so that a transmission wave of one frame illustrated in FIG. 4, for example, is transmitted.

After the transmission wave is transmitted in step S11, the controller 10 performs control so that a reflected wave that is the transmission wave reflected off an object is received from the reception antenna 31 of the electronic device 1 (step S12).

After the reflected wave is received in step S12, the controller 10 determines whether a body movement of a person located around the electronic device 1 is detected based on the transmission wave and the reflected wave (step S13).

In step S13, the controller 10 may perform the distance FFT processing and the velocity FFT processing on a beat signal based on the transmission wave and the reflected wave. In this case, the distance FFT processing unit 11 may perform the distance FFT processing, and the velocity FFT processing unit 12 may perform the velocity FFT processing. The oscillation source extracting unit 15 may determine whether a body movement such as a heartbeat in a human body is detected based on the results of the distance FFT processing and the velocity FFT processing.

After a body movement such as a heartbeat in a human body is detected in step S13, at least one of the controller 10 or the phase control units 23 perform control such that a beam is formed in a direction of the detected body movement, that is, beamforming is performed (step S14).

After the beam is formed in the direction of the body movement in step S14, the controller 10 detects a heartbeat of the person from the body movement toward which the beam is directed (step S15). In general, when a weak oscillation such as a heartbeat is detected with a radio wave, a detection range tends to be narrow. However, the electronic device 1 performs beamforming in a direction of the detected body movement and thus can detect a weak body movement such as a heartbeat in a human body with good accuracy.

After a heartbeat is detected in step S15, the controller 10 performs control so that the beam of the transmission waves tracks the subject with the body movement (step S16).

In step S16, the controller 10 may perform control so that the beam tracks the subject with the body movement in accordance with, for example, an algorithm below. That is, first, a covariance matrix is determined based on a recursive least squares (RLS) algorithm represented by Expressions (2) to (5) below by using time-series data of an antenna IQ signal obtained after 2D FFT is performed on a reflected wave reflected by the detected subject. In Expressions below, ν denotes a forgetting factor and k denotes time.

[Math. 1]
$$\hat{h}(k+1) = \hat{h}(k) + k(k)e(k) \quad (2)$$

[Math. 2]
$$k(k) = \frac{v^{-1}P(k)x(k)}{1 + v^{-1}x(k)^T P(k)x(k)} \quad (3)$$

[Math. 3]
$$P(k+1) = v^{-1}P(k) - v^{-1}k(k)x(k)^T P(k) \quad (4)$$

[Math. 4]
$$e(k) = y(k) - \hat{h}(k)^T x(k) + n(k) \quad (5)$$

In Expressions above, Expression (6) below represents an L-dimensional gain vector.

[Math. 5]
$$k(k) \quad (6)$$

In Expressions above, Expression (7) below represents an inverse matrix (L×L matrix) of the covariance matrix of the input signal.

[Math. 6]
$$P(k) \quad (7)$$

The covariance matrix of the input signal above can be represented by Expression (8) below.

[Math. 7]
$$\left| \sum_{i=0}^{h} v^{k-1}x(i)x(i)^T \right| \quad (8)$$

After the covariance matrix is determined based on the RLS algorithm described above, a covariance matrix for which the detected subject moves at a next time point may be calculated. Then, a weight of the beam of the transmission waves is calculated by using a Wiener solution represented by Expression (9) below. In this way, the detected subject can be tracked.

[Math. 8]
$$W_{opt} = R_{xx}^{-1} r_{xs} \quad (9)$$

In Expression (9) above, $W_{opt}$ denotes an antenna weight by the Wiener solution. In Expression (9), $R_{xx}$ denotes P(k) described above. In addition, $r_{xs}$ is a response vector and denotes a correlation value (sample mean) between the phase and the amplitude for each antenna.

After the subject is tracked in step S16, the controller 10 may end the operation illustrated in FIG. 7.

On the other hand, if no body movement is detected in step S13, at least one of the controller 10 or the phase control units 23 may change the pattern of the beam of the transmission waves (step S17) and then end the operation illustrated in FIG. 7. In step S17, at least one of the controller 10 or the phase control units 23 may change the direction of the beam of the transmission waves, for example.

The operation illustrated in FIG. 7 may be performed repeatedly, for example, at predetermined timings or irregularly. For example, the operation illustrated in FIG. 7 may be performed repeatedly in units of frames of the transmission waves.

As described above, in the electronic device 1 according to the one embodiment, the controller 10 may detect a heartbeat of a subject that reflects a transmission wave, based on a transmission signal transmitted as the transmission wave and a reception signal received as a reflected wave. In the electronic device 1 according to the one embodiment, the controller 10 forms a beam of the transmission wave in a direction of the subject 200 (for example, a person) to detect a heartbeat of the subject 200. In this case, in response to detection of a body movement of a human body serving as the subject 200, the controller 10 may form a beam of the transmission wave in a direction in which the body movement is detected. In response to detection of the body movement of the human body serving as the subject 200, the controller 10 may control the beam of the transmission wave to track the body movement.

In the electronic device 1 according to the one embodiment, if a body movement of a human body serving as the subject 200 is not detected, the controller 10 may change a pattern of the beam of the transmission wave. In this case, if the body movement of the human body serving as the subject 200 is not detected, the controller 10 may change a direction of the beam of the transmission wave.

If a body movement of a human body is detected, the electronic device 1 according to the one embodiment performs beamforming in a direction in which the body movement is detected and thus can detect a heartbeat. If a body movement of a human body is not detected, the electronic device 1 according to the one embodiment changes a pattern of the beam to change the direction of beamforming and thus can perform detection of a body movement again. Thus, the electronic device 1 according to the one embodiment can detect a heartbeat in a human body or the like through transmission and reception of a radio wave.

As described above, the electronic device 1 according to the one embodiment detects a weak oscillation such as a heartbeat by using, for example, a millimeter-wave sensor including a plurality of transmission antennas and a plurality of reception antennas. If a subject is not detected, the electronic device 1 according to the one embodiment detects a body movement of the subject by performing a beamforming pattern with the transmission antennas while changing transmission phases of the antennas. On the other hand, if a body movement of the subject is detected, the electronic device 1 according to the one embodiment detects a heartbeat by performing beamforming in a direction of the body movement. As described above, the electronic device 1 according to the one embodiment automatically detects a direction of a human body, and thus can improve a signal quality. Therefore, the electronic device 1 according to the one embodiment can improve a heartbeat detection accuracy and/or a heartbeat detection range. Thus, the electronic device 1 according to the one embodiment can detect a heartbeat of a person with high accuracy.

While the present disclosure has been described based on the various drawings and the embodiments, it is to be noted that a person skilled in the art can easily make various variations or corrections based on the present disclosure.

Therefore, it is to be noted that these variations or corrections are within the scope of the present disclosure. For example, functions and the like included in each functional unit can be rearranged without causing any logical contradiction. Multiple functional units or the like may be combined into one or may be divided. The embodiments according to the present disclosure described above are not limited to strict implementation according to the respective embodiments described above, and may be implemented by appropriately combining the features or omitting part thereof. That is, a person skilled in the art can make various variations and corrections to the contents of the present disclosure based on the present disclosure. Therefore, these variations and corrections are within the scope of the present disclosure. For example, in each embodiment, each functional unit, each means, each step, or the like can be added to another embodiment or replaced with each functional unit, each means, each step, or the like in another embodiment without causing any logical contradiction. In each embodiment, multiple functional units, means, steps, or the like may be combined into one or may be divided. In addition, the embodiments according to the present disclosure described above are not limited to strict implementation according to the respective embodiments described above, and may be implemented by appropriately combining the features or omitting part thereof.

The embodiments described above are not limited to implementation as the electronic device 1. For example, the embodiments described above may be implemented as a method for controlling a device such as the electronic device 1. For example, the embodiments described above may be implemented as a program executed by a device such as the electronic device 1.

REFERENCE SIGNS 1 electronic device
10 controller
11 distance FFT processing unit
12 velocity FFT processing unit
13 determining unit
14 angle-of-arrival estimating unit
15 oscillation source extracting unit
16 oscillation component extracting unit
17 oscillation waveform converting unit
18 heartbeat data extracting unit
20 transmission unit
21 signal generating unit
22 synthesizer
23 phase control unit
24 amplifier
25 transmission antenna
30 reception unit
31 reception antenna
32 LNA
33 mixer
34 IF unit
35 AD conversion unit

The invention claimed is:

1. An electronic device comprising:
a transmission antenna unit including phase control units and a plurality of transmission antennas and configured to transmit a transmission wave;
a reception antenna configured to receive a reflected wave that is the transmission wave having been reflected; and
a controller configured to detect a heartbeat of a subject that reflects the transmission wave, based on a transmission signal transmitted as the transmission wave and a reception signal received as the reflected wave, wherein the controller is configured to form a beam of the transmission wave by controlling a phase of each of the phase control units to form the beam of the transmission wave in a direction of the subject to detect a heartbeat of the subject, and the controller is configured to, in response to detection of body movement of a human body serving as the subject, control the beam of the transmission wave to track the body movement by calculating an inverse matrix of a covariance matrix of an input signal, and a weight of the beam of the transmission wave by using a value calculated by using a correlation value between a phase and an amplitude of each antenna.

2. The electronic device according to claim 1, wherein the controller is configured to, in response to detection of a body movement of the human body serving as the subject, form a beam of the transmission wave in a direction in which the body movement is detected.

3. The electronic device according to claim 1, wherein when the body movement of the human body serving as the subject is not detected, change a pattern of the beam of the transmission wave.

4. The electronic device according to claim 3, wherein the controller is configured to, when the body movement of the human body serving as the subject is not detected, change a direction of the beam of the transmission wave.

5. The electronic device according to claim 1, further comprising:

a storage unit that is configured to store a correlation between a direction of beamforming and amounts of phase by which the respective transmission signals transmitted by the plurality of transmission antennas are to be controlled.

6. A method for controlling an electronic device, comprising:

transmitting a transmission wave from a transmission unit including phase control units and a plurality of transmission antennas;

receiving, from a reception antenna, a reflected wave that is the transmission wave having been reflected;

detecting a heartbeat of a subject that reflects the transmission wave, based on a transmission signal transmitted as the transmission wave and a reception signal received as the reflected wave;

forming a beam of the transmission wave by controlling a phase of each of the phase control units to form the beam of the transmission wave in a direction of the subject to detect a heartbeat of the subject; and in response to detection of body movement of a human body serving as the subject, controlling the beam of the transmission wave to track the body movement by calculating an inverse matrix of a covariance matrix of an input signal, and a weight of the beam of the transmission wave by using a value calculated by using a correlation value between a phase and an amplitude of each antenna.

7. The method according to claim 6, further comprising:

storing a correlation between a direction of beamforming and amounts of phase by which the respective transmission signals transmitted by the plurality of transmission antennas are to be controlled.

8. A program for causing an electronic device to execute:

transmitting a transmission wave from a transmission unit including phase control units and a plurality of transmission antennas;

receiving, from a reception antenna, a reflected wave that is the transmission wave having been reflected;

detecting a heartbeat of a subject that reflects the transmission wave, based on a transmission signal transmitted as the transmission wave and a reception signal received as the reflected wave;

forming a beam of the transmission wave by controlling a phase of each of the phase control units to form the beam of the transmission wave in a direction of the subject to detect a heartbeat of the subject; and in response to detection of body movement of a human body serving as the subject, controlling the beam of the transmission wave to track the body movement by calculating an inverse matrix of a covariance matrix of an input signal, and a weight of the beam of the transmission wave by using a value calculated by using a correlation value between a phase and an amplitude of each antenna.

9. The program according to claim 8, further causing electronic device to execute:

storing a correlation between a direction of beamforming and amounts of phase by which the respective transmission signals transmitted by the plurality of transmission antennas are to be controlled.

* * * * *